United States Patent [19]
Junk et al.

[11] Patent Number: 5,830,763
[45] Date of Patent: Nov. 3, 1998

[54] PROCESS FOR PREPARING DEUTERIUM TAGGED COMPOUNDS

[76] Inventors: Thomas Junk, 5141 Everett Dr., Baton Rouge, La. 70809; W. James Catallo, 4630 Tulane Dr., Baton Rouge, La. 70808

[21] Appl. No.: 746,100

[22] Filed: Nov. 6, 1996

[51] Int. Cl.$^6$ .................................................. G01N 37/00
[52] U.S. Cl. .............................................................. 436/56
[58] Field of Search .................................. 436/56, 57, 60, 436/140

[56] References Cited

U.S. PATENT DOCUMENTS

| | | | |
|---|---|---|---|
| 5,525,516 | 6/1996 | Krutak et al. | 436/56 |
| 5,665,538 | 9/1997 | Slater et al. | 436/56 X |
| 5,710,046 | 1/1998 | Rutledge et al. | 436/56 |

OTHER PUBLICATIONS

Yao, J. et al "Deuteration of Extremely Weak Organic Acids by Enahnced Acid–Base Reactivity in Supercritical Deuteroxide Solution" J. Am. Chem. Soc. vol. 116, pp. 11229–11233, 1994.

Werstiuk, N.H. et al "The Hight Temperature and Dilute Acid (HTDA) Procedure as a General Method of Replacing Aromatic Hydrogen by Deuterium" Can. J. Chem. vol. 52, pp. 2169–2171, 1974.

Junk, T.H. et al. "Preparative Supercritical Deuterium Exchange in Arenes and Heteroarenes" Tetrahedron Letters, vol. 37, No. 20, pp. 3445–3448, May 13, 1996.

*Primary Examiner*—Jeffrey Snay
*Attorney, Agent, or Firm*—Richard J. Hammond

[57] ABSTRACT

A process for the preparation of organic and inorganic deuterium-tagged compounds is disclosed. The process comprises heating a deuterium oxide-solution of an organic or inorganic compound, the solution having a pH of from about 10 to about 1 to a temperature and pressure so that a supercritical reaction mass forms and one or more deuterium atoms of the deuterium oxide solvent exchanges with one or more protons of the organic or inorganic compound. After cooling the reaction solution formed from the supercritical reaction, the organic or inorganic deuterium-tagged compound is separated.

5 Claims, No Drawings

PROCESS FOR PREPARING DEUTERIUM TAGGED COMPOUNDS

FIELD OF THE INVENTION

This invention relates to a method for identifying a source of chemical mixtures, especially petroleum, that are released into the environment by the steps of determining the composition of the source of such mixture, selecting from such determination a portion of the composition representing compounds having a heavy semi-volatile fraction and a portion of the composition representing compounds having a light semi-volatile fraction, adding to the source of such mixture one or more compound that are deuterated and represent the heavy semi-volatile fraction and the light semi-volatile fraction and determining the composition of the petroleum source having the deuterated compounds added thereto.

Methods to prepare the deuterated compounds in sufficient quantity for determining the source of the chemical mixture using such deuterated compounds that represent the heavy semi-volatile fraction and the light semi-volatile fraction are also disclosed.

BACKGROUND OF THE INVENTION

The bulk transportation of petroleum raw materials, intermediates and finished products as well a waste compositions containing petroleum residues typically involves the release, i.e., spilling, either accidentally or purposefully, of such materials into the environment. The actual source of the release of these materials may be difficult to identify due to possibility of multiple sources or that the releasing source may have long ago fled the scene. However, it is recognized that the source of these releases must be identified. Insurance indemnification, risk management, legal, environmental and legislative considerations play a significant part in such assessments.

The classical method used to determine the source of a petroleum spill has been by chemical analysis of the residue remaining in the environment. Typically, this is accomplished by isolating selected compounds from the residual mixture of chemicals and determining their ratios. The ratios then are claimed to provide a "fingerprint" of the petroleum source.

While the fingerprint approach noted above, has been used widely, e.g. in the Exxon Valdez spill, it has received considerable criticism because of its lack of quantitation, relying on interpretation of the data in attributing sources to any developed chemical profile. At best, the fingerprinting protocol offers an order-of-magnitude resolution in concentration determination and does not rely to any great extent on extensive external standardization. Thus, while a difference of 10 parts can be distinguished from 100 parts of a compound, 10 parts versus, for example 60 parts can not with confidence. Since the analysis depends on ratios of materials, these errors produce sufficient uncertainty to make any conclusions almost equivalent to educated guesses. In fact, where a spill can be attributed to multiple sources ( diesel, pipeline, automobile, etc.) and weathering of the spilled mixture has occurred, the fingerprinting method is so unreliable that it should not be used.

As disclosed in U.S. Pat. No. 5,474,937 one of the methods recognized a useful in eliminating the qualitative fingerprinting and similar methods is to "code" or "tag" the petroleum mixture before any transport occurs. The tag must be stable, detectable, non-denaturing, nonhazardous and specific to the materials being tagged. Additionally, these tagged compounds must share the physical and chemical properties of the untagged compounds so that environmental considerations are not altered. However, once tagged the composition can be traced with very high confidence. Thus, a unique, bar coded-type of mixture could result that not effect quality or performance of the product but would accompany the product for monitoring purposes if dumped or spilled. However, while this patent identifies petroleum as one of the materials useful for incorporating tagged compounds, the materials disclosed as useful tags are light hydrocarbons, which are relatively volatile and not representative of many petroleum materials being transported.

For petroleum products the types of materials useful in the bar code tagging approach noted above are those compounds that are already present in the petroleum mixture, but are altered in some fashion to produce an acceptable, unique bar code-type of tag. Thus, tagged, for example deuterated, compounds that represent light volatile fractions and those representing heavy volatile fractions appear to offer unique compositions for adding to petroleum sources that may be subject to spills. These compounds should, as observed above, be similar to the compounds in the petroleum source to which they will added. Deuterated compounds such as 1-methylnaphthalene, 1,2-dimethylnaphthalene, m-xylene, etc. are ideal since when added to the petroleum material in know ratios would provide a unique bar code and thereby unequivocally identify the petroleum mixture to which they had been added. Unfortunately, these compounds are difficult to prepare and so expensive that their use for any commercial tagging purposes is precluded. In fact, they are not commercially available.

Methods to prepare deuterated aromatics that fit the parameters outlined above as useful in tagging and bar coding petroleum mixtures have been disclosed.

Werstiuk et al has disclosed a method of replacing aromatic hydrogen by deuterium. See Can. J. Chem., 52, 2169(1974).

Hsiao et al, Lipids, 9(11), 913 (1974) prepared fully deuterated fatty acids at atmospheric pressure by proton exchange with deuterium gas over palladium on charcoal catalyst.

An extensive survey of hydrogen isotope exchange of various organic compounds in liquid ammonia has been published. The article contains little information regarding deuteration of petroleum-related aromatics. See Shatenshtein, *Advances In Physical Organic Chemistry*, pp 155–201, 1963. Deuterium exchange of aromatics in super critical water has been reported by Yao et al, J. Amer. Chem. Soc., 116, 1129 (1994); and Townsend, et al, ind. Eng. Chem. Res., 27 143 (1988). The former publication reports relatively low levels of deuteration and the latter required catalytic means to achieve significant deuterated products.

Accordingly, it is an object of the present invention to provide a method to identify the source of petroleum materials, including crude oil and refined petroleum products as well as petroleum intermediates and petroleum waste products.

It is a further object of the present invention to provide a method to identify the source of a petroleum material by adding to such material compounds that are representative of aromatic compounds already present in the petroleum material but are deuterated.

It is an additional object of the present invention to provide a method of deuterating aromatic compounds using supercritical deuterium oxide ($D_2O$) as the reaction medium.

These and other objects of the present invention are set forth as more fully described in the following description.

DESCRIPTION OF THE PREFERRED EMBODIMENTS

In one embodiment of the present invention, a method for identifying a petroleum source is disclosed. The petroleum subject to identification in accordance with the present invention is any natural or refined liquid or semi-liquid hydrocarbon material further characterized as, for example, mineral oil, rock oil, earth oil, seneca oil, crude oil, naphtha, etc. being additionally classified as having boiling points between about 18° and over 300° C. and melting points between about 38° to about 80° C.

Preferably, petroleum as used herein includes crude oil and the fractions of crude oil boiling between about 60°–200° C. (gasoline) to about 300° C. and above (heavy lubrication oil).

In practicing the method of the present invention, it is first necessary to determine the chemical identity of the petroleum material that is subject to the identification process. While several analytical methods can be used for identification procedure involving petroleum hydrocarbons, the most accurate of the methods is by the use of gas chromatographic and/or mass spectrographic procedures. These procedures for characterization of petroleum materials and the instruments associated with such procedures are well known in the prior art. For example, see Giger et al, Anal. Chem., 46, 1163 (1974) and 40 CFR, Chap. 1, Part 136, Appendix A, Method 625 (Jul. 7,1997 Edition).

Preferably, the method of the present invention used to first characterize the petroleum material involves first fractionating the petroleum product into fractions separated by their boiling points, i.e., by distillation. The semi-volatile fractions can be readily isolated from asphaltenes by extraction with a suitable solvent such as benzene, dichloromethane, etc. The isolated fractions are then typically analyzed by a gas chromatograph—mass spectrograph (GC-MS) instrument, which further "fractionates" (by GC) and identifies (by mass) the constituents of the mixture. One or more target compounds are selected in the light, semi-volatile part of the GC-MS scan and in the heavy, semi-volatile part of the scan. Deuterated analogs of the targeted compounds are then prepared and used as the bar-code identifiers of the present invention.

As noted above, the typical mixture of compounds in common petroleum sources is quite complex. However, the compounds in these mixtures are well known and their position in the array of compounds in the petroleum mixture is not difficult to determine. For example, naphthalene has a molecular weight of 128.17 and a boiling point of 217.7° C. It's position in a mixture of aromatics of similar molecular weights can be determined by adding a known amount of naphthalene to the mixture being analyzed. The enhanced peak in the chromatogram (compared to the original) identifies this compound.

In the process of the present invention, the compounds added to the petroleum source under consideration are deuterated aromatic compounds. While any deuterated aromatic or alkyl-substituted aromatic compound is useful in carrying out the objectives of the present invention, it is preferred that more than one deuterated aromatic compound are added to the petroleum source. The preferred selection of deuterated compounds to be added are one or more compounds from the lower boiling fractions and one or more compounds from the higher boiling fractions. These fractions as noted above are termed semi-volatile fractions and are particularly identified as light, semi-volatile fractions (having a mass number between about 128–200) and heavy semi-volatile fractions (having a mass number between about 200–350). In the process of the present invention, it is critical to have both heavy and light semi-volatile deuterated aromatic compounds present that are substantially the same as compounds already existing in the petroleum source. Because of the variety of conditions that the petroleum source will encounter during transit and when exposed to the environment, transformations may occur in the composition of the petroleum source that should also effect the deuterated material. For example, if a petroleum material is spilled containing both light and heavy semi-volatile fractions additionally tagged with substantially identical deuterated aromatic compounds, the effects of time, salt water, heat, etc. may destroy or dilute the concentration of the light semi-volatile fraction to the point that it can not be detected. The heavy semi-volatile fraction may form tar balls, that retains the tagged, bar-coded materials. Identification of the source of the petroleum forming such tar balls, i.e. by GC/mass spec, is assured since the amounts of deuterated compounds are already known.

Once the selection of the deuterated compounds has been made, these compounds (preferably produced according to the supercritical process disclosed in greater detail herein), are added to the petroleum source. The method of addition is conventional in nature and is typically simply by physically mixing a known quantity of the deuterated aromatics with the petroleum substrate. Should the petroleum material be in a storage tank, pouring the deuterated mixture into the stored\ material will result in adequate mixing of the deuterated compounds into the petroleum source within a few hours. Naturally, pumping or transporting will ensure that a uniform mixture results.

The amount of deuterated materials added to the petroleum source is dependent upon the level protonated homologues found in the original sample. However, concentrations of deuterated compounds in the range of about 1 microgram to 1 gram, preferably about 0.1 mg to about 0.1 gram,. Most preferably about 1 mg to about 10 mg per milliliter of mixture are used in the method of the present invention.

Accordingly, once the deuterated "tagged" compounds are added, that petroleum source can be readily identified, even when admixed with other petroleum sources or subject to evaporation or, environmental or other degradation. This is particularly the case because the proton-bearing (naturally-occurring) species and the deuterium-bearing (the bar-coded) homologs partition and behave identically in the environment.

The preferred method to manufacture the deuterated compounds used in the method of the present invention is by the supercritical deuterium oxide ($SD_2O$) process.

As noted previously, deuterations in supercritical deuteroxide solutions have been disclosed. While the prior art shows successful deuteration of a number of aromatic compounds, the yields of such deuterated compounds, especially halogenated aromatic compounds, are either negligible or impractically low. Further, a very high pH (about pH 14) is required for these reactions. Under supercritical conditions, these high pH deuterium oxide solutions are extremely corrosive to the vessels used to contain the deuterium exchange reactants. Reaction times must therefore be kept to a minimum to avoid rupture of the reaction vessel. Because of such short reaction periods, equilibrium conditions are rarely reached. Accordingly, yields of deuterated product and the percentage of such product that has been deuterated are disadvantageously effected.

The SD$_2$O process of the present invention is a high pressure process typically carried out in a sealed tube or an autoclave capable of withstanding pressures of up to about 12,000 psi and temperatures of up to about 500° C. Deuterium oxide (about 99.9% isotopically pure) is added to the tube (or autoclave) and a well-dried sample of the compound to be deuterated is added. After sealing the reaction vessel to which theses components are added and heating to the temperatures noted previously, a supercritical reaction mass is formed.

Contrary to the teachings of the prior art, the process of the present invention can be carried out at an unexpectedly low pH, i.e., at a pH of from about 1 to about 10, preferably from about 1 to about 6.9, most preferably from about 1 to about 5.0. In cases where a pH of over 7 is required, an alkali metal or alkali earth metal deuteroxide (sodium or potassium deuteroxide is preferred) is added. As noted, the tube (or autoclave) is sealed and heated to about 500° C. for a time necessary for the deuterium exchange reaction to proceed to completion, e.g. preferably about 1, most preferably about 7 hours. Lower temperatures are possible, but reaction times are prolonged. Longer times may be necessary in cases where the substrate is not easily deuterated, e.g., up to about 72 hours.

Ratios of compound to be deuterated (by weight) to amount of deuterium oxide from about 0.1 to 100, preferably from about 0.5 to 50, most preferably from about 1 to 10. In many cases, it is highly preferred to have a 50:50 mixture (by weight) of compound to be deuterated to deuterium oxide. When the alkali metal hydroxide is used, it is added in a catalytic amount at about 0.1% to about 1.0% by weight of the total solution. After cooling, the tube (autoclave) is opened and the deuterated product separated from the reaction mass. Separations may be achieved by conventional means, e.g., by distillation, chromatography, etc. Final yields of deuterated product are at least 50%, achieving a % deuteration of greater than 90%.

The compounds susceptible to deuteration according to the process of the present invention, are organic or inorganic compounds bearing protons capable of exchange with deuterium under supercritical conditions. Thus numerous aliphatic, aromatic, heteroaromatic and mixed alkyl, aryl or heteroaryl compounds with or without functional groups, can be successfully used in this process. Such compounds include organic compounds that are: aromatic and heteroaromatic as well as the alkyl and halo-substituted derivatives thereof, e.g., benzene, naphthalene, thiophene, α-methylnaphthalene, 1,4-dichlorobenzene, etc.; diaryl and diheteroarylethers as well as the alkyl-and halo-substituted derivatives thereof, e.g., diphenylether, difurylether, 4,4'-dimethyldiphenylether, etc.; diaryl and diheteroarylsulfides, e.g., diphenylsulfide, etc.; phenols and the alkyl- and halo-substituted phenols, e.g., phenol, 4-chlorophenol, etc., cresols and the alkyl-and halo-substituted cresols, e.g., o-cresol, 2-hydroxy-3-methyl-4-ethylbenzene; xylenols and the alkyl and halo-substituted xylenols; dibenzo-p-dioxanes and the alkyl- and halo-substituted dibenzo-p-dioxanes; etc. Similarly, numerous ammonium or ammonium-containing inorganic compounds are useful herein.

Illustrative of the compounds deuterated by the process of the present invention are (% isolated yield, % deuteration):

1,3.5-trimethylbenzene-d$_{12}$ (76,>96)
1-methylnaphthalene-d$_{10}$ (75,>97)
1,2-dimethylnaphthalene-d$_{12}$ (74,>97)
phenanthrene-d$_{10}$ (82,>98)
3-methylphenanthrene-d$_{12}$ (85,>97)
3,9-dimethylphenanthrene-d$_{14}$ (83,>96)
benzo[f]quinoline-d$_9$ (82,>97)
phenanthridine-d$_9$ (64,>85)
dibenzothiophene-d$_8$ (80,>97)
isobutylbenzene-d$_8$ (76, aromatic>97)
n-butlybenzene-d$_7$ (60,>97)
aniline-d$_7$ (78,>97)

It should be noted that, while the specification discloses the specific embodiment of a method for identifying a petroleum source by using a deuterated compound, the method of the present invention also encompasses other embodiment that comprise the use of a deuterated compound made by the supercritical process as disclosed herein, and employed as tags or markers for substrates other than petroleum.

The following examples are illustrative of the process of the present invention but are in no way intended to limit its scope.

EXAMPLES

Example 1

A 50 ml autoclave was charged with 1.5 g of diphenylamine and 20 g deuterium oxide. The pH was neutral (pH 7). This mixture was heated to 395±10° C. for 8 hours (supercritical conditions). After cooling, the partially deuterated diphenylamine was collected by filtration.

The material recovered by filtration above was subjected to a second supercritical deuteration, after which was recovered 1.36 g of [2,2',4, 4'6,6'-d$_6$] diphenylamine with >95% isotopic purity at the deuterated positions.

Example 2

A 50 ml autoclave was charged with 1.5 g of 2-methylnaphthalene, 0.3 g of calcium oxide and 20 g of deuterium oxide. This mixture was heated to supercritical conditions at 400±10° C. for 16 hours. After cooling, deuterated 2-methylnaphthalene was collected by extraction with 20 ml dichloromethane. Concentration of the extracted solution by evaporation produced 1.3 g of deuterated [1,3, 4,5,6,7,8α,α,α-d$_{10}$]-2-methylnaphthalene having an isotopic purity of 90%.

Example 3

A 50 ml autoclave was charged with 1.5 g of 2-methylnaphthalene, 19 g of deuterium oxide and 1 g of [d$_3$]phosphoric acid 85% in deuterium oxide. This mixture was heated to supercritical conditions, 400±10° C., for 16 hours. After cooling, 1.2 g of deuterated [1,3,4,5,6,7,8-α,α,α-d$_{10}$]-2-methylnaphthalene, isotopic purity >90%, were collected by filtration.

We claim:

1. A process for the producing a deuterated inorganic or organic compound comprising heating a deuterium oxide solution of an organic or inorganic compound said solution having a pH of from about 10 to about 1 to a temperature and pressure so that a supercritical reaction mass forms and one or more deuterium atoms of said deuterium oxide exchanges with one or more protons of said organic or inorganic compound;

separating from said deuterium oxide solution said deuterium-tagged organic or inorganic compound.

2. The process according to claim 1 wherein said pH is from about 1 to about 6.9.

3. The process according to claim 2 wherein said compound is an organic compound.

4. The process according to claim 3 wherein said organic compound is selected from the group consisting of aliphatic, aromatic, heteroaromatic and mixed alkyl, aryl or heteroaryl compounds with or without functional groups.

5. The process according to claim 4 wherein said organic compound is 1,3.5-trimethylbenzene, 1-methylnaphthalene, 1,2-dimethylnaphthalene, phenanthrene, 3-methylphenanthrene, 3,9-dimethylphenanthrene, benzo[f]quinoline, phenanthridine, dibenzothiophene, isobutylbenzene, n-butylbenzene or aniline.

* * * * *